(12) United States Patent
Pederson et al.

(10) Patent No.: US 8,721,698 B2
(45) Date of Patent: May 13, 2014

(54) LIGHT THERAPY DEVICE

(75) Inventors: Larry V. Pederson, Redmond, WA (US); Clayton G. Coffey, Medicine Hat (CA); Henry Hudema, Medicine Hat (CA)

(73) Assignee: The Litebook Company Ltd., Medicine Hat (CA)

( * ) Notice: Subject to any disclaimer, the term of this patent is extended or adjusted under 35 U.S.C. 154(b) by 0 days.

(21) Appl. No.: 13/488,920

(22) Filed: Jun. 5, 2012

(65) Prior Publication Data

US 2012/0245660 A1  Sep. 27, 2012

Related U.S. Application Data

(63) Continuation of application No. 13/344,068, filed on Jan. 5, 2012, now Pat. No. 8,453,651, which is a continuation of application No. 10/980,272, filed on Nov. 4, 2004, now Pat. No. 8,104,481, which is a continuation of application No. 09/710,782, filed on Nov. 13, 2000, now Pat. No. 6,875,225.

(51) Int. Cl.
*A61N 5/06* (2006.01)

(52) U.S. Cl.
USPC .............................. 607/90; 607/88

(58) Field of Classification Search
USPC ...................... 607/88–91; 128/898
See application file for complete search history.

(56) References Cited

U.S. PATENT DOCUMENTS

| | | | |
|---|---|---|---|
| 4,858,609 A | 8/1989 | Cole | |
| 4,946,452 A | 8/1990 | Py | |
| 5,149,184 A * | 9/1992 | Hughes et al. | 362/1 |
| 5,197,941 A * | 3/1993 | Whitaker | 600/27 |
| 5,274,403 A | 12/1993 | Gott | |
| 5,447,527 A | 9/1995 | Waldman | |
| 5,447,528 A | 9/1995 | Gerardo | |
| 5,503,637 A | 4/1996 | Kyricos et al. | |
| 5,545,192 A | 8/1996 | Czeisler et al. | |
| 5,782,895 A | 7/1998 | Zarate et al. | |
| 5,800,479 A | 9/1998 | Thiberg | |
| 5,820,625 A | 10/1998 | Izawa et al. | |
| 5,824,024 A | 10/1998 | Dial | |
| 5,879,155 A | 3/1999 | Kittelsen | |
| 5,919,217 A | 7/1999 | Hughes | |
| 5,923,398 A | 7/1999 | Goldman | |
| 6,135,117 A | 10/2000 | Campbell et al. | |

(Continued)

FOREIGN PATENT DOCUMENTS

| CA | 2300569 | 3/2000 |
|---|---|---|
| CA | 2317319 | 8/2000 |

(Continued)

OTHER PUBLICATIONS

Inexpensive ganzfield light therapy for relaxation, meditation, depression; http://www.morningstarlight.com/pricing.html, Nov. 27, 1999.

(Continued)

*Primary Examiner* — Ahmed Farah
(74) *Attorney, Agent, or Firm* — Bennett Jones LLP

(57) ABSTRACT

A light therapy device is taught including a light emitting assembly having light emitting diodes (LEDs) as a light source. The light emitting assembly capable of generating 2,500 lux to 7,500 lux at 12 inches.

16 Claims, 3 Drawing Sheets

(56) References Cited

U.S. PATENT DOCUMENTS

| | | | |
|---|---|---|---|
| 6,164,787 | A | 12/2000 | Seki et al. |
| 6,167,648 | B1 | 1/2001 | Dimmick |
| 6,235,046 | B1 | 5/2001 | Gerdt |
| 6,299,632 | B1 | 10/2001 | Jaillet |
| 6,350,275 | B1 | 2/2002 | Vreman et al. |
| 6,443,977 | B1 | 9/2002 | Jaillet |
| 6,488,698 | B1 | 12/2002 | Hyman |
| 8,104,481 | B2 * | 1/2012 | Pederson et al. ............. 128/898 |
| 2001/0056293 | A1 | 12/2001 | Brainard |
| 2002/0198576 | A1 | 12/2002 | Chen et al. |
| 2003/0069616 | A1 | 4/2003 | Skene et al. |

FOREIGN PATENT DOCUMENTS

| | | |
|---|---|---|
| CA | 2403314 | 9/2001 |
| DE | 296 00 470 | 5/1996 |
| WO | WO 91/14475 | 10/1991 |

OTHER PUBLICATIONS

Description of the Technology; Morning StarLight; Morning StarLight Light Therapy System for Seasonal Affective Disorder, SAD, Meditation, Relaxation; Nov. 27, 1999.

The Practical Method to Prevent Jet Lag Based on Breakthrough Research; Jet Lag Calculator; Bio-Brite, Inc. © 1994.

Light Therapy Products; Products, Lamps—LightTherapy Products; http://www.lighttherapyproducts.com/products_lamps/html, Jan. 2, 1999.

Northern Light Technologies, The SADELITE.

Information on (sub-) seasonal affective disorder and Bright Light; Phillips.

R.W. Lam and A.J. Levitt; Canadian Consensus Guidelines for the Treatment of Seasonal Affective Disorder: A Summary of the Report of the Canadian Consensus Group on SAD; http://www-ths.mcmaster.ca/direct/sad2.html. Aug. 19, 1999.

C.E. Reme et al, Bright light therapy in focus: lamp emission spectra and ocular safety; Technology and Health Care 4 (1996) 403-413 IOS Press.

Outside In's Home Page; Outside In Home Page : Info on SAD, Body Clock, Jetlag, Winter Depression and Light; http://www.outsidein.co.uk/index.htm; Jun. 19, 1999.

Uplift Day-Light; Brighten your Day . . . Uplift your Workspace.

Light: An Essential Part of Your Life; Day-Lights . . . Light Systems for Better Living From: DayLight Technologies, Inc.; Toronto, Canada.

G.C. Brainard et al; Action Spectrum for Melatonin Regulation in Humans: Evidence for a Novel Circadian Photoreceptor; The Journal of Neuroscience, Aug. 15, 2001, 21(16): 6405-6412.

V.L. Warman et al; Phase advancing human circadian rhythms with short wavelength light; Neuroscience Letters 342 (2003) 37-40; www.elsevier.com/locate/neulet.

LightTherapy hHealing force through light; http://www.samarit.ch/lighttherapy.htm, Nov. 15, 2002.

R.W. Lam and A.J. Levitt; Clinical Guidelines for the Treatment of Seasonal Affective Disorder; 1999; Clinical & Academic Publishing; Canada.

I.Hecker et al. Preventing Jet Lag, Bio-Brite Inc. © 1995.

Litebook™website http://www.litebook.com/htdocs/lightwell/faq.html, Nov. 15, 2002.

Litebook™ brochure, product available Mar. 20, 2001.

Atlantic Horizon—Products Page; Verseo Mini Mood Saver, http://www.verseo.com/ . . . May 9, 2003.

Lite Pad Mood Saver—Buy it here; Lighten your Mood!, http://www.shoplifestyle.com/ . . . , Apr. 17, 2003.

goLITE Mood Relief, Sep. 2003.

Light Therapy Solutions—Golite, http://lighttherapy.com/golite.html, Jun. 10, 2003.

* cited by examiner

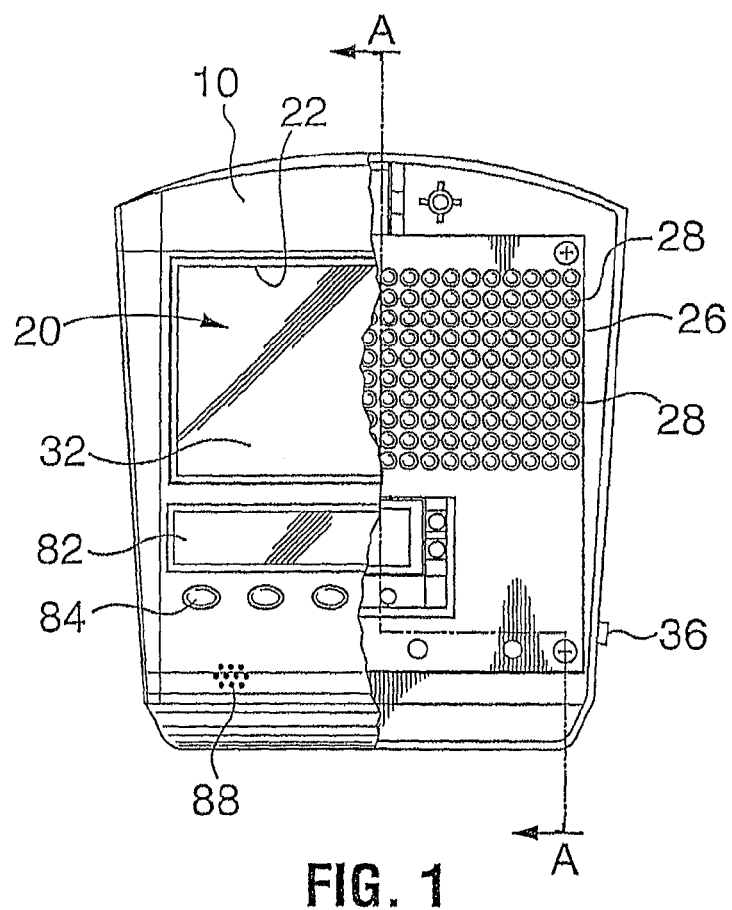
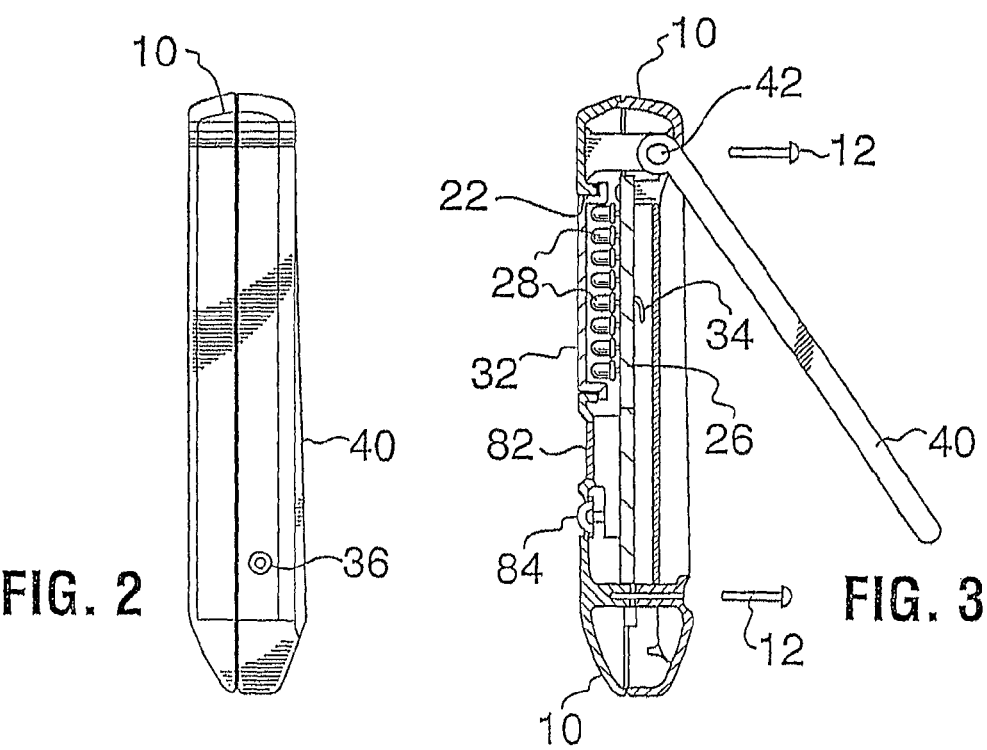
FIG. 1
FIG. 2   FIG. 3

LIGHT THERAPY DEVICE

CROSS REFERENCE TO RELATED APPLICATIONS

This application is a continuation application of U.S. Ser. No. 13/344,068 filed Jan. 5, 2012 which is presently pending. U.S. Ser. No. 13/344,068 is a continuation application of U.S. application Ser. No. 10/980,272 filed Nov. 4, 2004, now, U.S. Pat. No. 8,104,481 issued Jan. 31, 2012. U.S. application Ser. No. 10/980,272 is a continuation of U.S. application Ser. No. 09/710,782 filed Nov. 13, 2000, now U.S. Pat. No. 6,875,225 issued Apr. 5, 2005. The parent applications and the present application claim priority to Canadian patent application No. 2,300,569 filed Mar. 14, 2000 and to Canadian patent application No. 2,317,319 filed Aug. 30, 2000.

FIELD OF THE INVENTION

The present invention relates to a light therapy device and in particular to a light therapy device for treatment of light deficient disorders.

BACKGROUND OF THE INVENTION

There is much support for the use of light therapy to overcome light deficient disorders. It has been proven that treatments involving shining light directly towards a patient's eyes will alleviate or cure light deficient disorders including Seasonal Affective Disorder (SAD), circadian sleep disorders and circadian disruptions associated with jet-lag, shift-work, PMS and bulimia.

There are two types of light therapy devices presently available. One type of device is large in size and floor or desk mountable. These devices include light sources of fluorescent bulbs. Although they can be moved from one position to another, they are not generally portable. In addition, the light source is quite fragile. The second kind of light therapy devices is head mountable. These devices are formed as eyeglasses or visors. While they are portable, they are not generally accepted by patients for use in public because of their odd appearance when worn on the head. This combined with safety concerns about eye damage given the proximity of the light source to the eye, has resulted in head mountable treatment devices failing to be generally accepted as a light therapy device.

These devices therefore are of limited use for persons requiring a portable and discreet treatment device. A light therapy device is needed for use by, for example, the business traveler that is portable and aesthetically appealing.

SUMMARY OF THE INVENTION

The present invention provides a portable and lightweight hand-held light therapy device. The device is durable, being resistant to damage by normal transport. The device uses light emitting diodes (LEDs) as a source of light. LEDs offer a light source that is lightweight, small in size, simple, durable as well as energy efficient. The device is useful for travel and for in-flight use while being aesthetically acceptable.

In accordance with one aspect of the present invention, there is provided a light treatment comprising: an outer housing including a opening; a light emitting assembly in the housing and operable to emit light through the opening in the housing, the light emitting assembly including a plurality of LEDs capable of generating 2,500 lux to 7,500 lux at 12 inches.

The LEDs include at least some capable of emitting whitelight. In one embodiment, the LEDs are arranged in a pattern over an area and the light emitting assembly is selected to emit light from the LEDs along a substantially straight line directly toward the user. Preferably, a diffuser screen of light diffusing sheet material is positioned over the LEDs to provide a more uniform emission of light. While LEDs do not emit any significant amount of ultraviolet radiation, the diffuser sheet material can include a UV filter, if desired.

The outer housing can include a first member and a second member, the first member and the second member being releasably locked together and the light emitting assembly being storable in the first member and being mountable on the housing such that the housing acts as a base to support the light emitting assembly. In one embodiment, the first and second members are pivotally connected and openable in a manner similar to a book. The first and second members, when closed enclose an inner compartment accessible by opening the first and second members about their pivotal connection. The light emitting assembly is storable in the inner compartment. In this embodiment, the light emitting assembly can be mountable on the first member and the second member can act as a base.

To facilitate therapy using the device, the housing can also accommodate a therapy calculator for determining a treatment regime based on an input of information.

BRIEF DESCRIPTION OF THE DRAWINGS

FIG. 1 is a front elevation view of a light therapy device according to the present invention. A portion of the device has been cut away to facilitate illustration of internal components.

FIG. 2 is a side elevation view of the light therapy device of FIG. 1 with the support leg folded against the housing.

FIG. 3 is a sectional view along line A-A of FIG. 1.

DETAILED DESCRIPTION OF THE PREFERRED EMBODIMENTS

Figure 4:
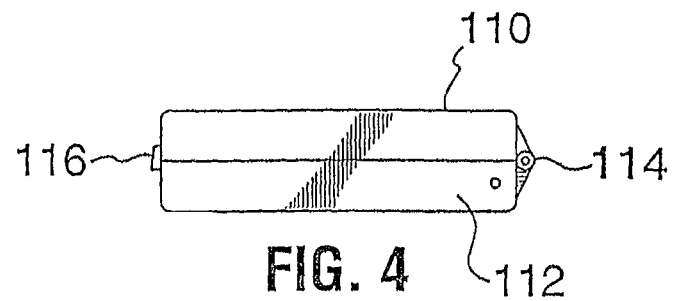
FIG. 4 is a side elevation view of another light therapy device according to the present invention in a closed configuration.

Referring to FIGS. 1 to 3, a light therapy device according to one embodiment of the present invention is shown. The device is small in size and resembles a large calculator or hand-held computer. Preferably, the outside dimensions of the device are less than about 7 inches wide, 7 inches high and 1.5 inches deep. The size can be varied as desired and with consideration as to portability, convenience and the components that must be contained therein.

The device includes an outer housing 10. The housing is preferably formed of a durable, impact resistant material such as, for example, a polymer (i.e. nylon, thermoplastic or blends thereof). Preferably, all housing parts are of minimal thickness to provide suitable impact resistance and support for internal components while minimizing the weight of the device. The housing can be formed, as shown, in parts secured together by screws 12 or other fastening means.

The housing carries a light emitting assembly 20. The light emitting assembly is mounted in the housing such that in operation light emitted therefrom is directed out through an opening 22 in the housing.

Light emitting assembly 20 includes a printed circuit (PC) board 26 providing electrical connection for light emitting diodes 28. The LEDs are spaced apart on the board, with consideration as to their light output and wavelength, such that the assembly emits a light of illumination adequate for treatment of light deficient disorders. In particular, the light emitting assembly generates adequate illumination for treatment of light deficient disorders including Seasonal Affective Disorder (SAD), circadian sleep disorders and circadian disruptions associated with jet-lag, shift-work, PMS and bulimia, which is between 2,500 and 7,500 lux, and preferably between about 3,500 and 5,500 lux at 12 inches from the assembly. To generate this level of illumination, the assembly generally includes between about 10 and 150 LEDs together having a total light output of between 50 and 500 candelas and preferably about 250 to 450 candelas. The number of LEDs in the light emitting assembly may be reduced considerably as the efficiency of a LED is increased.

Using a light therapy device according to the present invention, treatments of acceptable duration can be administered. As an example, treatments for SAD can be completed in ¼ to 4 hours and in most cases, ½ to 3 hours.

For bright-light therapy, preferably white LEDs are used. However, it is sometimes useful to combine light of different wavelengths and in some instances to approximate the spectral properties or distribution of a tropical sunrise. Therefore, LEDs 28 can be entirely of the type emitting white light or, alternatively, LEDs emitting light of various wavelengths (i.e. red or amber) can be used with white light emitting diodes. The light generated by the light emitting assembly is preferably constant, though it may also be pulsed.

In one embodiment, a diffuser screen 32 is mounted over the diodes to create a more uniform, less harsh light emission. Preferably, LEDs 28 are mounted a suitable distance from diffuser screen 32 such that the light emitted by each LED overlaps on the screen and avoids the appearance of individual points of light behind the screen. If a diffuser screen is used, it is necessary to ensure that adequate levels of light, as set out above, are passed therethrough to permit treatment.

Power is supplied to the LEDs through electrical lines 34. Power can be provided through batteries or preferably, to reduce weight, through a jack 36 for connection to a 120v electrical supply (for use in North America). The device preferably operates using DC power and is supplied with an external AC-DC converter. Since the device is particularly useful during long distance travel in the treatment of jet lag, an adapter can be provided within the device or separately for device compatibility with foreign voltages of AC power or with DC power, as is provided through power ports mounted in aircraft armrests.

To facilitate light treatment, a support leg 40 can be provided for supporting the housing in a propped position such that light is emitted in a generally horizontal direction. In one embodiment, support leg 40 is connected by a hinge 42 to the rear of the housing such that the leg can be rotated between a supporting position and a stored position against the rear of the housing. A more complex stand for elevating the light illuminating assembly can be used, as desired.

The light treatment device can be mounted in a vehicle passenger compartment including, for example, a passenger or operator seat area. The vehicle can be, for example, an aircraft, a train, a bus, a truck or an automobile. In one embodiment, the light treatment device is mounted in an aircraft seat back or in an aircraft seat armrest for use by air travelers. The device can be mounted in a manner similar to aircraft telephones, individual video monitors, and other such devices, wherein the light treatment device is attached to an adjustable extension arm, thereby enabling the user to remove the light treatment device from an armrest and position it appropriately for treatment. Alternately, the light treatment device may be temporarily removed from its seat back mounting position and positioned on a tray table or other surface for treatment, while remaining secured to the seat back by means of a cable that could also serve as a power source. The device may also be mounted into an airliner flight deck or other such areas of an airliner to provide discreet and convenient light treatments for pilots, flight attendants and other such on-board crew affected by jet lag and fatigue.

In another embodiment, the light treatment device can be mounted in the passenger compartments of vehicles, for example, automobiles, transport trucks, buses, trains, and other such vehicles, wherein the device is stored when not in use but readily available to provide a light therapy treatment. In the case of automobiles and trucks, the device may be mounted on the underside of a sun visor, or within the glove compartment, or under the vehicle's dashboard. In the latter two examples, the device can be attached to an adjustable extension arm in order to permit proper positioning for treatment.

The device may also be mounted so as to provide a light treatment for the driver or operator of these vehicles, with appropriate precautions being indicated for safe operation of the vehicle, for example, at those times when the vehicle is parked or idle. One such embodiment is described hereinafter with reference to FIG. 7.

Figure 5:
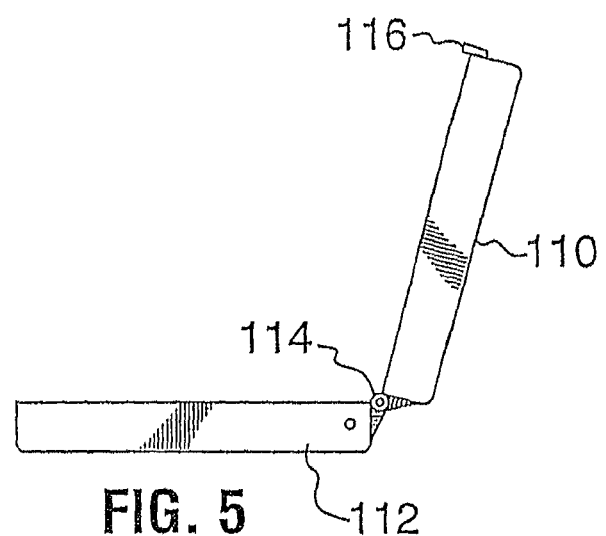
FIG. 5 is a side elevation view of the device of FIG. 4 in an open configuration, ready for use.
Figure 6:
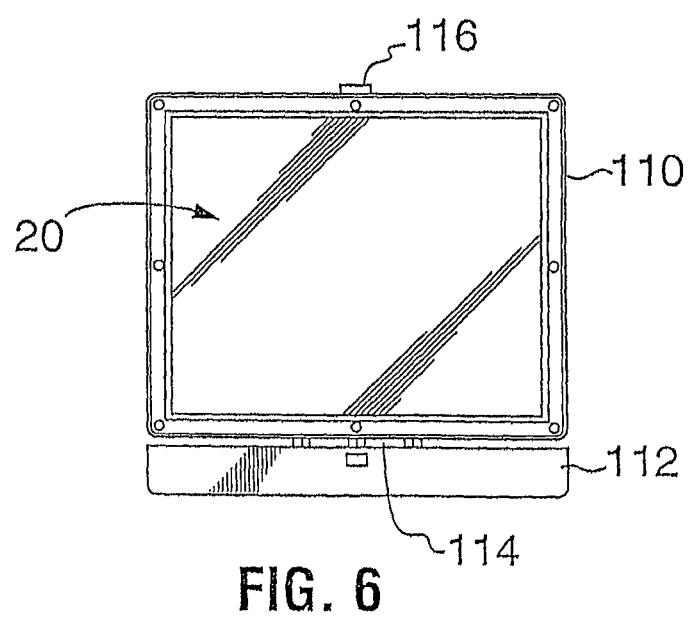
FIG. 6 is a front elevation of the device and configuration of FIG. 5.

Housing 10 can also be formed to accommodate other electronics, batteries etc. or to define storage space such as for cords, adapters, glasses or other items. The housing can also include a cover or a case. Referring to FIGS. 4 to 6, a light therapy device according to another embodiment of the present invention is shown. The device has an outer housing including an upper housing member 110 and a lower housing member 112. The housing members are connected by a hinge 114 that permits them to pivot relative to each other between a closed position shown in FIG. 4 and an open position shown in FIGS. 5 and 6. When in the closed position, the housing members can be releasably locked together by a catch 116. The device is small in size and, when closed, resembles a portable compact disc player or a make-up compact.

The housing encloses a light emitting assembly 20. In the illustrated embodiment, light-emitting assembly 20 is mounted in the upper housing member. The light emitting assembly is mounted on the inwardly facing portion of the upper housing member so that, when the device is in the closed position, assembly 20 is protected within the housing members. In this way, the light emitting assembly, which is more fragile than the housing, is protected against damage during transport.

The device is opened for use to administer a light treatment. In a preferred embodiment, upper housing member 110 unfolds from the closed position by rotating about hinge 114. Lower housing member 112 acts as a base for supporting the light emitting assembly. Preferably, hinge 114 is of the type that permits self-locking in at least a few rotational orientations. The use of such a hinge permits that, for example, upper housing member can be oriented to direct the light downwardly, horizontally or, if preferred, in other directions. This is useful as it may be necessary, depending on the treatment, to have the light directed into the patient's eyes or alternately downwardly toward a workspace.

Counterweights (not shown) can be mounted in the lower housing member to prevent the device from tipping. Member 112 can also be formed to accommodate electronics, batteries etc. or to define storage space such as for cords, adapters, glasses or other items. Member 112 can also accommodate a treatment calculator, as will be described hereinbelow.

In one embodiment illustrated, for example in FIGS. 1 to 3, housing 10 also accommodates a calculator including a display 82, a key pad 84 and a processor mounted within housing 10. The calculator is programmed to calculate a light treatment regime based on input of information. The calculator processor uses calculation references such as that known as the Jet Lag Calculator™ available from Bio-Brite, Inc., Maryland. In one embodiment, the calculator can be used to calculate light treatment regimes for jet lag based on inputs of information, as follows:

Option 1
 i. Number of time zones crossed during trip
 ii. Direction of time zones crossed (East or West)
 iii. Normal wake-up time of patient (for establishing the patient's "body clock")

Option 2
 i. Departure city
 ii. Arrival city
 iii. Normal wake-up time of patient Based on the input of the above-noted information, the calculator will then calculate and display a treatment regime including, for example, a period of light exposure and a period of light avoidance. In option 2, the calculator determines the number of time zones through which travel will occur and uses this to calculate treatment regime. The calculator in one embodiment calculates a two-day treatment regime.

In one embodiment, the calculator keypad includes keys to be depressed when inputting particular information. As an example, the keypad can include keys such as: "departure city", "destination city" and "wake up time". The calculator can be adapted to prompt the patient such as by displaying questions requesting the appropriate information. Preferably, the calculator includes a pause function capable of recording a time of treatment interruption and capable of outputting from memory the portion of the treatment remaining when treatment is resumed.

In addition or alternately, the calculator can be programmed for calculation of other treatment regimes such as, for example, for treatments to alleviate fatigue in shift workers. Treatments for shift workers may include inputs such as work shift start time, previous shift time and normal waking time.

A speaker 88 is preferably provided for communication to the user. As an example, the speaker can communicate with the calculator processor to audibly prompt a user to input information. In addition, the speaker can function to emit an audible signal, such as an alarm, to alert a user to commence or modify a treatment. In one embodiment, the calculator processor controls a switch for the light emitting assembly such that it is turned on or off in response to a signal from the processor.

In a preferred embodiment, the calculator memory is capable of storing previous treatment regimes. These stored treatment regimes can be recalled from processor memory for repeat trips or shift work schedules.

If desired, to enhance the usefulness of the device, the calculator can also be programmed with other information including a clock, a standard mathematical calculator or other information such as an address book, etc.

Figure 7:
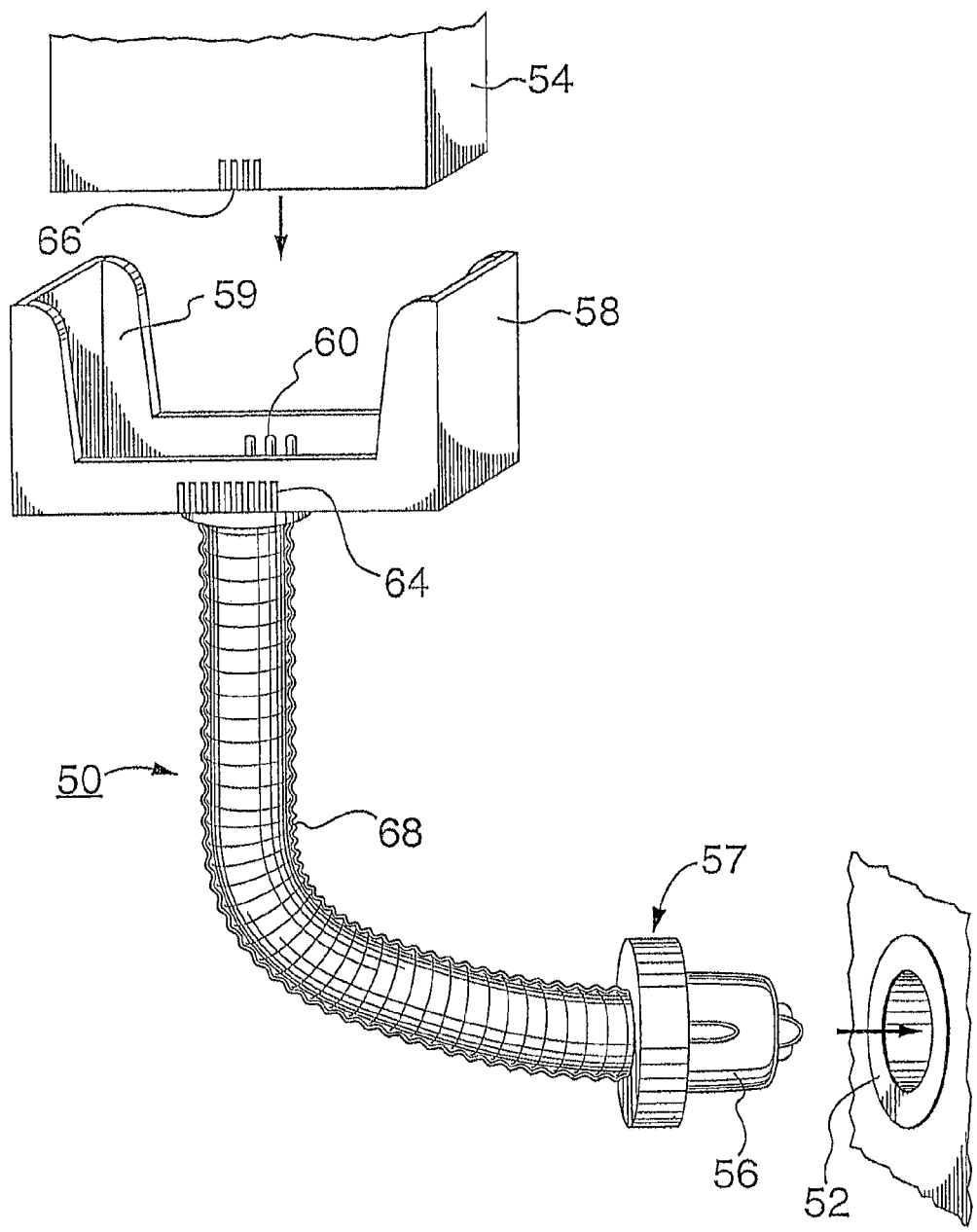
FIG. 7 is an elevation of a device for permitting mounting of a light therapy device in a passenger compartment of a vehicle. The device is aligned for insertion into a power port of a vehicle and a light therapy device is aligned for insertion into the docking bay of the device.

As noted hereinbefore, a light therapy device according to the present invention can be mounted in a vehicle for use by passengers. One such embodiment is illustrated in FIG. 7. A vehicle mounting adaptor 50 useful for mounting a light treatment device in a vehicle passenger compartment acts as an interface between the vehicle power port 52 (i.e. an in-dash cigarette lighter) and the light treatment device 54. In particular, at one end the adaptor has a power port contactor 56 for insertion into the power port. A locking collar 57 is threadedly engaged at the outboard end of the contactor 56. Once power port contactor 56 is inserted into power port 52, locking collar 57 can be tightened down about the port by threaded advancement to reinforce the engagement between port 52 and power port contactor 56.

At the opposite end, the adapter includes a docking port 58 with a recess 59 having therein electrical contactors 60. The light treatment device is mountable in the recess of docking port 58 in electrical communication with contactors 60. Venting slots 64 are formed through the docking port and positioned to substantially align with the vents 66 on light treatment device 54 to provide ventilation to the light treatment device therethrough.

Power cables (cannot be seen) extend between ends 56 and 58 to provide electrical communication therebetween. The power cables are housed within a bendable arm 68 of the type including a corrugated tube and internal supports that can be bent into various orientations and, once positioned, will hold fast in that orientation. Arm 68 is bendable yet rigid enough to hold the weight of the light treatment device 54 and docking port 58 without moving out of the bended configuration into which it has been adjusted. Locking collar 57 also securely holds power port contactor 56 in power port 52 even against the weight of the light treatment device and against the stress of bending arm 68. Adapter 50 can be removed from power port 54 and stored when not required.

Numerous modifications, variations and adaptations may be made to the particular embodiments of the invention described above without departing from the scope of the invention as defined in the claims.

The embodiments of the invention in which an exclusive property or privilege is claimed are defined as follows:

1. An ocular light therapy device for administering an ocular light treatment to a user with a light deficient disorder, the ocular light therapy device comprising:
 an outer housing including an opening, the outer housing including a width, a height and a depth, the width and the height each being greater than the depth and the width and the height defining dimensions of a front face in which the opening is positioned;
 a support configured to support the housing in a treatment position on a support surface spaced from the user;
 a light emitting assembly in the housing and operable to emit light through the opening in the housing, the light emitting assembly including an LED light source configured to generate an output of light suitable for the ocular light treatment of the light deficient disorder;
 a diffuser screen of light diffusing sheet material positioned to diffuse light from the LED light source passing through the opening;
 a treatment selector for setting a treatment regime; and
 a processor within the housing for storing the treatment regime, the processor being configured to accept input from the treatment selector and the processor being configured to turn off the light emitting assembly after administering the ocular light treatment according to the treatment regime.

2. The ocular light therapy device of claim 1 wherein the light emitting assembly includes between about 10 and 150 LEDs.

3. The ocular light therapy device of claim 1 wherein the emitted light has an intensity of 50 to 500 candelas.

4. The ocular light therapy device of claim 1 wherein the treatment selector is configured to pause and resume the ocular light treatment.

5. The ocular light therapy device of claim 1 wherein the processor is configured to administer the light for ¼ to 4 hours according to the treatment regime.

6. The ocular light therapy device of claim 1 wherein the processor is configured to calculate the treatment regime in response to an input from the treatment selector.

7. The ocular light therapy device of claim 1 wherein the treatment selector is configured to permit input to the processor of (i) a number of time zones crossed, (ii) a direction of travel and (iii) a normal wake-up time.

8. The ocular light therapy device of claim 1 wherein the treatment selector is configured to permit input to the processor of (i) a departure city, (ii) an arrival city and (iii) a normal wake-up time.

9. The ocular light therapy device of claim 1 wherein the outer housing is sized to be hand held.

10. The ocular light therapy device of claim 9 wherein the width is less than about 7 inches, the height is less than about 7 inches and the depth is less than about 1.5 inches.

11. The ocular light therapy device of claim 1 wherein the light deficient disorder is a circadian sleep disorder.

12. The ocular light therapy device of claim 1 wherein the light deficient disorder is a circadian disruption.

13. The ocular light therapy device of claim 1 wherein the light deficient disorder is Seasonal Affective Disorder.

14. The ocular light therapy device of claim 1 wherein the light deficient disorder is jet lag.

15. The ocular light therapy device of claim 1 wherein the light deficient disorder is bulimia.

16. The ocular light therapy device of claim 1 wherein the light deficient disorder is PMS.

* * * * *